United States Patent [19]

Koe

[11] Patent Number: 5,061,728

[45] Date of Patent: Oct. 29, 1991

[54] USE OF 4-PHENYL-1,2,3,4-TETRAHYDRO-1-NAPH-THALENAMINE DERIVATIVES IN THE TREATMENT OF INFLAMMATION AND AS IMMUNOSUPPRESSANTS

[75] Inventor: B. Kenneth Koe, Gales Ferry, Conn.

[73] Assignee: Pfizer Inc., New York, N.Y.

[21] Appl. No.: 622,308

[22] Filed: Dec. 5, 1990

Related U.S. Application Data

[62] Division of Ser. No. 320,014, Mar. 7, 1989, Pat. No. 4,981,870.

[51] Int. Cl.$^5$ .................... A61K 31/13; A61K 31/20; A61K 31/135; A61K 31/275
[52] U.S. Cl. ............................ 514/520; 514/557; 514/646; 514/657
[58] Field of Search ............... 514/520, 557, 646, 657

*Primary Examiner*—S. Friedman
*Attorney, Agent, or Firm*—Peter C. Richardson; Paul H. Ginsburg; Robert F. Sheyka

[57] ABSTRACT

4-Phenyl-1,2,3,4-tetrahydro-1-napthalenamine derivatives have been found useful for the treatment of psychosis, inflammation and as immunosuppressants.

13 Claims, No Drawings

USE OF 4-PHENYL-1,2,3,4-TETRAHYDRO-1-NAPHTHALENAMINE DERIVATIVES IN THE TREATMENT OF INFLAMMATION AND AS IMMUNOSUPPRESSANTS

This is a division of application Ser. No. 320,014, filed on Mar. 7, 1989, now U.S. Pat. No. 4,981,870.

BACKGROUND OF THE INVENTION

The present invention relates to the use of 4-phenyl-1,2,3,4-tetrahydro-1-naphthalenamine derivatives in the treatment of psychosis, inflammation and as immunosuppressants.

U.S. Pat. No. 4,536,518 discloses cis-4-phenyl-1,2,3,4-tetrahydro-1-naphthalenamine derivatives useful as antidepressants.

U.S. Pat. No. 4,566,676 discloses trans-4-phenyl-1,2,3,4-tetrahydro-1-naphthalenamine derivatives useful as antidepressants.

It has now been discovered that the compounds disclosed in the aforementioned U.S. patents have sigma receptor binding activity and are therefore useful in the treatment of psychosis, inflammation and as immunosuppressants.

SUMMARY OF THE INVENTION

The present invention relates to a method of achieving an antipsychotic, antiinflammatory or immunosuppressive effect in a mammal in need of such treatment comprising administering to said mammal an antipsychotic, antiinflammatory or immunosuppressive effective amount of a compound of the formula:

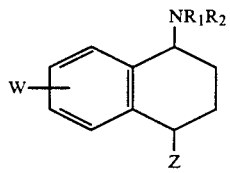

or a pharmaceutically acceptable acid addition salt thereof, wherein
$R_1$ is selected from the group consisting of hydrogen and $C_1$–$C_3$ alkyl,
$R_2$ is $C_1$–$C_3$ alkyl,
Z is

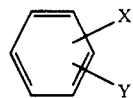

wherein X and Y are independently selected from the group consisting of hydrogen, fluoro, chloro, bromo, trifluoromethyl, alkoxy of from 1 to 3 carbon atoms and cyano, with at least one of X and Y other than hydrogen; and
W is selected from the group consisting of hydrogen, fluoro, chloro, bromo, trifluoromethyl and alkoxy of from 1 to 3 carbon atoms.

The compounds of the formula I include both the cis and the trans isomers. In the cis isomer, the $NR_1R_2$ and Z moieties are both oriented on the same side of the cyclohexane ring. In the trans isomer, the $NR_1R_2$ and Z moieties are oriented on opposite sides of the cyclohexane ring. Because both the 1 and 4 carbons of Formula I are asymmetrically substituted, each cis compound and each trans compound has two optically active enantiomeric forms denoted, respectively, cis-(1R) and cis-(1S) and trans-(1R) and trans-(1S). The preponderance of the pharmaceutical activity of the cis-isomer compounds of the formula I resides in the (1S)-enantiomeric forms thereof, while the preponderance of pharmaceutical activity of the trans-isomer compounds of formula I resides in the (1S)-enantiomeric forms.

Preferred compounds or their pharmaceutically acceptable acid addition salts for use in the present invention are:
Cis-(1S) (4S)-N-methyl-4-(3,4,-dichlorophenyl)-1,2,3,4-tetrahydro-1-naphthalenamine;
Cis(1S) (4S)-N-methyl-4-(4-chlorophenyl)-1,2,3,4-tetrahydro-1-naphthalenamine;
Cis(1S) (4S)-N-methyl-4-(3-trifluoromethyl, 4-chlorophenyl)-1,2,3,4-tetrahydro-1-naphthalenamine;
Trans(1S) (1R)-N-methyl-4-(3,4-dichlorophenyl)-1,2,3,4-tetrahydro-1-naphthalenamine;
Trans(1R) (4S)-N-methyl-4-(3,4-dichlorophenyl)-1,2,3,4-tetrahydro-1-naphthalenamine;
Cis(1R) (4R)-N-methyl-4-(3,4-dichlorophenyl)-1,2,3,4-tetrahydro-1-naphthalenamine; and
Cis(1S) (4S)-amino-4-(3,4-dichlorophenyl)-1,2,3,4-tetrahydro-1-naphthalenamine.
Cis(1S) (4S)-N,N-dimethyl-4-(3,4-dichlorophenyl)-1,2,3,4-tetrahydro-1-naphthalenamine.

DETAILED DESCRIPTION OF THE INVENTION

The compounds of the formula I or the pharmaceutically acceptable acid addition salts thereof may be prepared and formulated as described in U.S. Pat. Nos. 4,556,676 and 4,536,518, the disclosures of which are hereby incorporated herein by reference.

The compounds of the formula I or the pharmaceutically acceptable acid addition salts thereof are useful in treating psychotic disorders in mammalian subjects (e.g. humans). For example, the compounds or salts are useful in treating psychotic disorders of the schizophrenic types, and especially for removing or ameliorating such symptoms and conditions as anxiety, agitation, tension, excessive aggression and social and/or emotional withdrawal, etc. that one normally encounters when dealing with psychotic patients.

The compounds of the formula I or the pharmaceutically acceptable salts thereof are also useful in treating inflammatory disorders in mammals (e.g. humans), including psoriasis, arthritis and inflammatory based diseases.

The compounds of the formula I or the pharmaceutically acceptable salts thereof are also useful as immunosuppressants.

Such compounds are useful in connection with transplant surgery and in treating conditions such as rheumatoid arthritis, lupus, and other autoimmune diseases or diseases characterized by immune hyperfunction.

For use as discussed above, the compounds of formula I or the pharmaceutically acceptable salts thereof may be administered to a subject in need of treatment by a variety of conventional routes of administration, including oral, by injection, topical, and in an aerosol carrier composition for administration by breathing.

In general, the compounds of the formula I and the pharmaceutically acceptable salts thereof are most desirably administered in doses ranging from about 0.1 mg. up to about 100 mg. per day, although variations will necessarily occur depending upon the weight and condition of the subject being treated and the particular route of pharmaceutical administration chosen. However, a dosage level that is in the range of from about 0.3 mg to about 10 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases, still larger doses may be employed without causing harmful side effects provided that such higher dose levels are first divided into several small doses for administration throughout the day.

Although the compounds of formula I can be administered alone, they will generally be administered in admixture with a pharmaceutical carrier selected with regard to the intended route of administration and standard pharmaceutical practice. For example, oral administration may be in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water. For parenteral injection, they may be used in the form of a sterile aqueous solution which may contain other solutes, for example enough salt or glucose to make the solution isotonic.

The antipsychotic, antiinflammatory and immunosuppressive activity of the compounds of the formula I and the pharmaceutically acceptable acid addition salts thereof is demonstrated by the following examples.

EXAMPLE 1

In Vitro Binding

Affinity of disclosed compounds for sigma receptors in brain tissue was ascertained by the degree of inhibition of binding of the sigma site radioligand, (+)-[$^3$H]3-(3-hydroxphenyl)-N-(1-propyl)piperidine ((+)-[$^3$H]3-PPP) in competition experiments in vitro. These experiments were conducted by the method of Largent et al. Proc. Nat. Acad. Sec. USA, 81 4983-87 (1984). Brains were removed from Sprague-Dawley CD male rats (Charles River Breeding Laboratories, Inc., Wilmington, Mass.; 200-300 g) following decapitation. Whole brain was homogenized in 25 volumes (v/w) of ice-cold 50 mM Tris (tris(hydroxymethyl)amino methane) hydrochloride pH 7.7 buffer using a Polytron PT-10 homogenizer. The pellet resulting from centrifugation of the homogenate at 45,000×g for 10 minutes at 0°-5° was washed twice by resuspension in the same volume of fresh buffer and recentrifugation. The final pellet was dispersed in 50 mM Tris hydrochloride pH 8.0 buffer (50 ml/g of original weight; "tissue preparation"). The incubation mixture in triplicate was comprised of 0.05 ml blank (10 µM pentazocine for nonspecific binding), test compound or vehicle; 0.20 ml (+)-[$^3$H]3-PPP (110 Ci/mmol, NEN ® DuPont; 3 nM final concentration) in 50 mM Tris hydrochloride pH 8.0 buffer; and 0.75 ml tissue preparation. The latter was added just prior to incubation of the mixture at 25° C. for 90 minutes. Afterwards, the mixture was diluted with 2.5 ml 10 mM Tris hydrochloride pH 7.7 buffer and filtered under vacuum through a Whatman GF/B glass-fiber filter (pretreated with 1% polyethyleneimine) in a Brandell cell harvester to recover the membranes. The filter was washed twice with the diluent buffer and placed in 10 ml Aquasol-2 (NEN ® DuPont Co.) for determination of bound radioactivity in a liquid scintillation counter. Percent inhibition of specific (+)-[$^3$H]3-PPP binding was calculated and the concentration inhibiting binding by 50% (IC$_{50}$) was determined.

EXAMPLE 2

In Vivo Binding

The efficacy of disclosed compounds for binding to brain sigma receptors in vivo was determined by comparing the labeling of these receptors in intact control and drug-pretreated mice with intravenously administered (+)-[$^3$H]3-PPP. These experiments were conducted by the method of Koe et al. Eur. J. Pharmacol. 1989, In press. Mice (male Swiss albino from Charles River Breeding Laboratories, Inc., Wilmington, Mass; 23-28 g) in groups of 5 received vehicle (controls) and 3 log doses of test compound intraperitioneally 30 minutes before an intravenous injection of (+)-[$^3$H]-PPP (400 µCi/kg). Five minutes later mice were killed by cervical dislocation and whole brains were removed and immediately frozen. Frozen brains were individually homogenized in 18 ml of ice-cold 50 mM Tris hydrochloride pH 8.0 buffer with a Polytron PT-10 homogenizer. Triplicate 1.0 ml aliquots were filtered under vacuum through Whatman GF/B filters to collect the membranes which were then washed with two 5-ml aliquots of 10 mM Tris hydrochloride pH 7.7 buffer. Membrane-bound radioligand (M) was determined by placing the filters in 10 ml Aquasol-R2 and measuring radioactivity in a liquid scintillation counter. Separate aliquots of the homogenates before filtration were assayed for total radioactivity (H) and protein content. The dose causing 50% inhibition of (+)-[$^3$H]3-PPP binding in vivo (ID$_{50}$) was estimated from semi-log plots of fraction bound (M/H), calculated as % control, versus dose.

TABLE 1

Inhibition of (+)-[$^3$H]3-PPP Binding

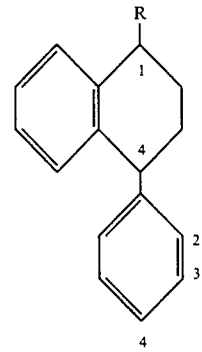

| Racemate | Substituents on Pendant Phenyl ring | R | IC$_{50}$ nM |
| --- | --- | --- | --- |
| (±)-trans | 4-F | NHCH$_3$ | 66 |
| (±)-cis | 4-Cl | NHCH$_3$ | 33 |
| (±)-trans | 4-Cl | NHCH$_3$ | 75 |
| (±)-cis | 3,4-diCl | NHCH$_3$ | 19 |
| (±)-trans | 3,4-diCl | NHCH$_3$ | 23 |
| (±)-cis | 3,4-diCl | N(CH$_3$)$_2$ | 44 |
| (±)-trans | 3,4-diCl | N(CH$_3$)$_2$ | 30 |

TABLE 1-continued

Inhibition of (+)-[³H]3-PPP Binding

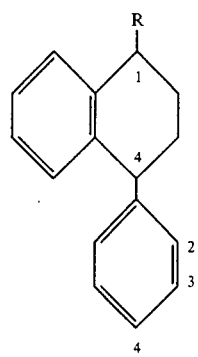

| Racemate | Substituents on Pendant Phenyl ring | R | IC$_{50}$ nM |
| --- | --- | --- | --- |
| (±)-cis | 2,4-diCl | NHCH$_3$ | 29 |
| (±)-cis | 4-Br | NHCH$_3$ | 13 |
| (±)-trans | 4-Br | NHCH$_3$ | 85 |
| (±)-trans | 3-CF$_3$ | NHCH$_3$ | 16 |
| (±)-cis | 4-CF$_3$ | NHCH$_3$ | 5.9 |
| (±)-trans | 4-CF$_3$ | NHCH$_3$ | 39 |
| (±)-cis | 3-CF$_3$, 4-Cl | NHCH$_3$ | 11 |
| (±)-trans | 3-CF$_3$, 4-Cl | NHCH$_3$ | 31 |

3 nM (+)-[³H]-3-PPP

TABLE 2

Inhibition of (+)-[³H]3-PPP Binding

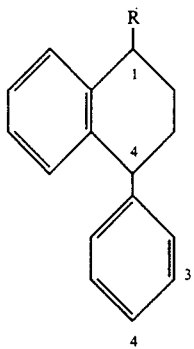

| Conformation | Substituents on Pendant Phenyl ring | R | IC$_{50}$ nM |
| --- | --- | --- | --- |
| (+)-1S, 4S | 4-Cl | NHCH$_3$ | 8.7 |
| (+)-1S, 4S | 3,4-diCl | NHCH$_3$ | 6.8 |
| (−)-1R, 4R | 3,4-diCl | NHCH$_3$ | 220 |
| (+)-1R, 4S | 3,4-diCl | NHCH$_3$ | 51 |
| (−)-1S, 4R | 3,4-diCl | NHCH$_3$ | 6.6 |
| (+)-1S, 4S | 3,4-diCl | N(CH$_3$)$_2$ | 28 |
| (+)-1S, 4S | 3,4-diCl | NH$_2$ | 58 |
| (+)-1S, 4S | 3-CF$_3$, 4-Cl | NHCH$_3$ | 17 |

3 nM (+)-[³H]3-PPP

TABLE 3

Inhibition of (+)-[³H]3-PPP Binding to Mouse Brain In Vivo

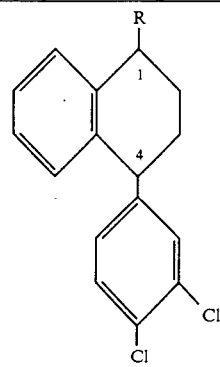

| Conformation | R | ID$_{50}$ mol/kg i.p. |
| --- | --- | --- |
| (+)-1S, 4S | NHCH$_3$ | 0.72 |
| (−)-1R, 4R | NHCH$_3$ | 17 |
| (+)-1R, 4S | NHCH$_3$ | 3.6 |
| (−)-1S, 4R | NHCH$_3$ | 0.43 |
| (+)-1S, 4S | NH$_2$ | 3.0 |

400 μCi/kg (+)-[³H]3-PPP i.v.

I claim:

1. A method of achieving an, antiinflammatory or immunosuppressive effect in a mammal in need of such treatment comprising administering to said mammal an, antiinflammatory or immunosuppressive amount of a compound of the formula:

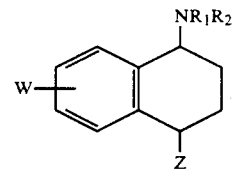

I or a pharmaceutically acceptable acid addition salt thereof, wherein
R$_1$ is selected from the group consisting of hydrogen and C$_1$-C$_1$ alkyl,
R$_2$ is C$_1$-C$_3$ alkyl,
Z is

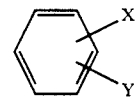

wherein X and Y are independently selected from the group consisting of hydrogen, fluoro, chloro, bromo, trifluoromethyl, alkoxy of from 1 to 3 carbon atoms and cyano, with at least one of X and Y other than hydrogen; and W is selected from the group consisting of hydrogen, fluoro, chloro, bromo, trifluoromethyl and alkoxy of from 1 to 3 carbon atoms.

2. A method according to claim 1 wherein said compound is the cis isomer.

3. A method according to claim 1 wherein said compound is the trans isomer.

4. A method according to claim 2 wherein said cis isomer is the (1S)-enantiomeric form.

5. A method according to claim 3 wherein said trans isomer is the (1S)-enantiomeric form.

6. A method according to claim 1 wherein said compound is Cis-(1S) (4S)-N-methyl-4-(3,4,-dichlorophenyl)-1,2,3,4-tetrahydro-1-naphthalenamine.

7. A method according to claim 1 wherein said compound is Cis(1S) (4S)-N-methyl-4-(4-chlorophenyl)-1,2,3,4-tetrahydro-1-naphthalenamine.

8. A method according to claim 1 wherein said compound is Cis(1S) (4S)-N-methyl-4-(3-trifluoromethyl, 4-chloro-phenyl)-1,2,3,4-tetrahydro-1-naphthalenamine.

9. A method according to claim 1 wherein said compound is Trans(1S) (1R)-N-methyl-4-(3,4-dichlorophenyl)-1,2,3,4-tetrahydro-1-naphthalenamine.

10. A method according to claim 1 wherein said compound is Trans(1R) (4S)-N-methyl-4-(3,4-dichlorophenyl)-1,2,3,4-tetrahydro-1-naphthalenamine.

11. A method according to claim 1 wherein said compound is Cis(1R) (4R)-N-methyl-4-(3,4-dichlorophenyl)-1,2,3,4-tetrahydro-1-naphthalenamine.

12. A method according to claim 1 wherein said compound is Cis(1S) (4S)-amino-4-(3,4-dichlorophenyl)-1,2,3,4-tetrahydro-1-naphthalenamine.

13. A method according to claim 1 wherein said compound is Cis(1S) (4S)-N,N-dimethyl-4-(3,4-dichlorophenyl)-1,2,3,4-tetrahydro-1-naphthalenamine.

* * * * *